US012781054B2

(12) United States Patent
Morone et al.

(10) Patent No.: US 12,781,054 B2
(45) Date of Patent: Nov. 3, 2026

(54) POLYMERIC (METH)ACRYLATE PHOTOINITIATORS

(71) Applicant: IGM RESINS ITALIA S.R.L., Milan (IT)

(72) Inventors: Marika Morone, Lipomo (IT); Vincenzo Razzano, Bussero (IT); Stefano Federico, Como (IT)

(73) Assignee: IGM RESINS ITALIA S.R.L., Milan (IT)

( * ) Notice: Subject to any disclaimer, the term of this patent is extended or adjusted under 35 U.S.C. 154(b) by 43 days.

(21) Appl. No.: 19/108,513

(22) PCT Filed: Sep. 28, 2023

(86) PCT No.: PCT/IB2023/059671
§ 371 (c)(1),
(2) Date: Mar. 4, 2025

(87) PCT Pub. No.: WO2024/074945
PCT Pub. Date: Apr. 11, 2024

(65) Prior Publication Data

US 2026/0071077 A1 Mar. 12, 2026

(30) Foreign Application Priority Data

Oct. 5, 2022 (IT) ........................ 102022000020481

(51) Int. Cl.

| | |
|---|---|
| ***C09D 4/00*** | (2006.01) |
| ***B29C 64/129*** | (2017.01) |
| ***B33Y 10/00*** | (2015.01) |
| ***B33Y 70/00*** | (2020.01) |
| ***C07C 65/36*** | (2006.01) |
| ***C07C 65/40*** | (2006.01) |
| ***C07C 229/52*** | (2006.01) |
| ***C07C 323/62*** | (2006.01) |
| ***C07D 209/86*** | (2006.01) |
| ***C07D 311/82*** | (2006.01) |
| ***C08F 222/20*** | (2006.01) |
| ***C09D 135/02*** | (2006.01) |
| *B29K 33/00* | (2006.01) |

(52) U.S. Cl.
CPC .............. *C09D 4/00* (2013.01); *B29C 64/129* (2017.08); *B33Y 10/00* (2014.12); *B33Y 70/00* (2014.12); *C07C 65/36* (2013.01); *C07C 65/40* (2013.01); *C07C 229/52* (2013.01); *C07C 323/62* (2013.01); *C07D 209/86* (2013.01); *C07D 311/82* (2013.01); *C08F 222/20* (2013.01); *C09D 135/02* (2013.01); *B29K 2033/08* (2013.01); *C08F 2800/20* (2013.01)

(58) Field of Classification Search
CPC .......... B29C 64/129; B33Y 10/00; C09D 4/00
See application file for complete search history.

(56) References Cited

U.S. PATENT DOCUMENTS

| | | | |
|---|---|---|---|
| 10,189,930 | B2 | 1/2019 | Van Den Bergen et al. |
| 2017/0029360 | A1 | 2/2017 | Gaudl et al. |

OTHER PUBLICATIONS

Search Report and Written Opinion of PCT/IB2023/059671 issued Nov. 30, 2023.

*Primary Examiner* — James Sanders
(74) *Attorney, Agent, or Firm* — Silvia Salvadori, P.C.; Silvia Salvadori

(57) ABSTRACT

The present invention relates to novel photoinitiators having improved reactivity and surface curing and/or lower post-cure yellowing and to photopolymerization compositions containing said photoinitiators. The invention also concerns a process for the photopolymerization of compositions comprising said photoinitiators as well as their use in articles of manufacture, including printed, coated, and fabricated assemblies.

12 Claims, No Drawings

POLYMERIC (METH)ACRYLATE PHOTOINITIATORS

The present invention relates to novel photoinitiators having improved reactivity and surface curing and/or lower post-cure yellowing and to photopolymerization compositions containing said photoinitiators. The invention also concerns a process for the photopolymerization of compositions comprising said photoinitiators as well as their use in articles of manufacture, including printed, coated, and fabricated assemblies.

PRIOR ART

In the last years, the design and the development of new photoinitiators (PIs) has been attracted increasing attention due to the large amount of photoinitiators that have been or are going to be banned as toxic or reprotoxic.

Various attempts were made to develop new photoinitiators able to mimic standard photoinitiators or to overcome problems such as yellowing, higher line speed, curing under LED lamps, some examples are glyoxylate 3-ketocoumarins (WO2021070152), benzoyl phenyltelluride PIs (Macromolecules, 2014, 47(16), 5526-5531), silicon based PIs (JP2010229169, Macromolecules, 2009, 42(16), 6031-6037, Macromolecules 2007, 40(24), 8527-8530, Macromol. Rapid Commun. 2017, 38, 1600470, Macromolecules, 2017, 50(17), 6911-6923), fluorine based PIs (US2019/0155153). For sensitive applications such as for example food packaging in addition to good reactivity and lower yellowing also photoinitiators able to photoreticulate in the matrix are preferred in order to avoid possible migration of the photoinitiators into the food.

Unfortunately, when used in standard applications, also these photoinitiators show some limitations, such as low surface curing and post-cure yellowing, which makes said PIs inappropriate in polymerizable systems involving transparent varnishes.

So, there exists the need of new technical solutions able to improve the surface curing of PIs without affecting the good reactivity of these products and/or to limit post-cure yellowing.

WO2015/010729 discloses polymeric photoinitiators containing a biphenyl group. We surprisingly found that the substitution of the biphenyl group with different organic moieties together with the addition of (meth)acrylate groups lead to a significant improvement in the performances of said PIs.

AIMS OF THE INVENTION

It is a first aim of the invention to provide for novel polymeric PIs, their use as photoinitiators and photocurable compositions comprising them.

It is a further aim of the invention to provide for photocurable compositions comprising the novel PIs of the invention.

Is a further aim of the invention to provide for processes for photocuring ethylenically unsaturated compounds using the novel PIs of the invention, as well as articles of manufacture made by said process.

DESCRIPTION OF THE INVENTION

According to one of its aspects, the present invention relates to a compound of formula (I)

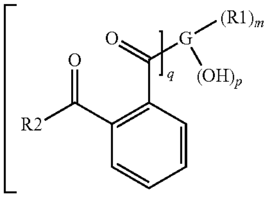

(I)

wherein

G is the residue of optionally ethoxylated and/or propoxylated monomeric, oligomeric or polymeric polyols G-(OH) m+q+p;

m is from 1 to 7 q is from 1 to 7;

p is from 0 to 6;

m+q+p is from 3 to 8;

R1 is $CH_2{=}CH{-}C({=}O)$ or $CH_2{=}C(CH_3){-}C({=}O)$;

R2 is selected from (A)

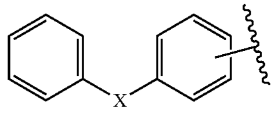

(B)

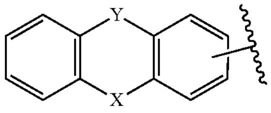

and (C)

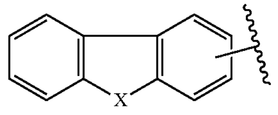

wherein

X is selected from O, S, C(R4)(R5) and NR7;

Y is selected from O, S, C(R4)(R5) and NR6;

R4 and R5 each independently, are selected from H, C1-C12 alkyl, OH and C1-C10 alkoxy;

R6 is selected from H, C1-C8 alky;

R7 is H, C1-C8 alkyl or unsubstituted phenyl;

and the wavy line shows the bonds linking to the keto groups of formula (I).

According to the invention, $G\text{-}(OH)_{m+q+p}$ is selected from a monomeric, an oligomeric, a polymeric polyol and mixtures thereof, which can be optionally ethoxylated or propoxylated.

Examples of suitable monomeric and oligomeric polyols are glycerol, di-glycerol, tri-glycerol, triethanolamine, trimethylol propane, di-trimethylol propane, pentaerythritol, dipentaeritrithol, sugar alcohols, such as sorbitol, mannitol and xylitol, mixtures thereof.

Examples of polymeric polyols are polyhydroxy polyethers, which can be both aliphatic or aromatic, polyhydroxy polyesters, polyhydroxy polyamides, polyhydroxy polyimides, polyhydroxy polycarbonates, styrene-allyl alcohols copolymers.

The alkoxylated polyols are particularly preferred for the realization of the present invention. Examples of such alkoxylated polyols are monomeric, oligomeric and polymeric polyols mentioned above, which have been alkoxylated, for example ethoxylated and/or propoxylated and/or butoxylated. Other suitable examples are linear or branched polyamines, which have been alkoxylated, and polyalkoxylated diamines, such as ethoxylated ethylene diamine and ethoxylated 1,3-propylene diamine. In the alkoxylated compounds of the invention, each group reactive toward the alkylene oxide can bring from 0 to 15 alkoxy units, preferably from 1 to 6 alkoxy units.

In a preferred embodiment $G\text{-}(OH)_{m+q+p}$ is selected from monomeric and oligomeric polyols.

In another preferred embodiment $G\text{-}(OH)_{m+q+p}$ is selected from monomeric and oligomeric polyols which have been ethoxylated and/or propoxylated.

Preferably, $G\text{-}(OH)_{m+q+p}$ has a number average molecular weight not greater than 1,500 Da, more preferably not greater than 1,000 Da and most preferably not greater than 800 Da; and and not lower than 100 Da, preferably not lower than 200 Da.

Preferably, $G\text{-}(OH)_{m+q+p}$ is selected from glycerol, ethoxylated and/or propoxylated glycerol, di-glycerol, ethoxylated and/or propoxylated di-glycerol, trimethylolpropane, ethoxylated and/or propoxylated trimethylolpropane, di-trimethylolpropane, ethoxylated and/or propoxylated di-trimethylolpropane, penthaerythritol, ethoxylated and/or propoxylated penthaerythritol, di-penthaerythritol, ethoxylated and/or propoxylated di-penthaerythritol, sorbitol, ethoxylated and/or propoxylated sorbitol, triethanolamine, and ethoxylated and/or propoxylated triethanolamine.

Preferably, m+q+p is from 3 to 8, and more preferably from 3 to 6, for instance 3, 4, 5 or 6.

Preferably, m is from 1 to 6 and more preferably from 1 to 4, for instance 1, 2, 3 or 4.

Preferably, q is from 1 to 6 and more preferably from 2 to 4, for instance 2, 3 or 4.

Preferably, p is from 0 to 6 and more preferably from 0 to 3, for instance 0, 1, 2 or 3.

When p is different from 0, compounds of Formula (I) have free alcoholic groups.

Mixtures of compounds of formula (I) are also included in the scope of the invention.

According to preferred embodiment, R1 is the residue of acrylic acid ($CH_2{=}CH{-}C({=}O)$).

According to preferred embodiment, R2 is (A) and X is S or O, preferably S.

According to preferred embodiment, R2 is (A) and X is N-phenyl.

According to preferred embodiment, R2 is (B), X is O and Y is $C(CH_3)(CH_3)$.

According to preferred embodiment, R2 is (C) and X is $CH_2$.

According to preferred embodiment, R2 is (C) and X is N-alkyl.

When X is S, oxidized forms of sulfur to sulfone or sulfoxide are also encompassed within the scope of the protection of the present invention.

According to another preferred embodiment of the present invention:

q is from 1 to 4, more preferably from 2 to 4, for instance 2, 3 or 4;

p is from 0 to 3, more preferably from 0 to 2, for instance 0, 1 or 2;

m is from 1 to 6, more preferably from 2 to 4, for instance 2, 3 or 4;

m+q+p is from 3 to 6 more preferably from 3 to 5, for instance 3, 4 or 5.

In the present description the expressions "alkyl" or "alkyl group" mean, where not differently indicated, a linear or branched, saturated alkyl chain containing the given number of carbon atoms and includes all possible isomer for each number of carbon atoms in the alkyl group, i.e. for three carbon atoms: n-propyl and isopropyl; for four carbon atoms: n-butyl, isobutyl and tertiary-butyl; for five carbon atoms: n-pentyl, 1,1-dimethyl-propyl, 2,2-dimethylpropyl and 2-methyl-butyl, etc.

Preferably, alkyl is C1-C4 alkyl, e.g. methyl or ethyl.

The compounds of the invention can be prepared according to any suitable process. For example, they can be prepared by Friedel-Crafts acylation and optionally an esterification according to Scheme 1 below:

Scheme 1

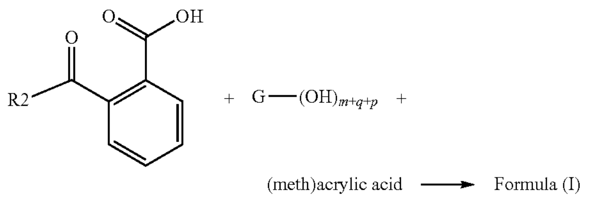

The reaction can be carried out in a suitable solvent, such as an aromatic solvent, for instance toluene and in the presence of methansulfonic acid and hypophosphorous acid. The resulting compound of Formula (I) may then be isolated according to known methods.

In the above reaction, (meth)acrylic acid may be substituted by a halide derivative, such as its chloride derivative.

The reactants are known and/or commercially available, or they can be prepared according to known methods and/or as disclosed in the Experimental Section which follows.

According to another of its aspects, the present invention relates to a process for the preparation of compounds of formula (I) which comprises performing the reaction according to Scheme 1 above.

The skilled in the art is perfectly able to perform the chemical reactions of Scheme 1, according to the known methods.

Details of the process of the invention are reported in the Experimental Section of the present description.

According to another of its aspects, the present invention relates to a photopolymerizable composition comprising:

a) from 50 to 99.9%, preferably from 70 to 98.9% by weight, based on the total content of the composition, of at least one ethylenically unsaturated compound;

b) from 1 to 40%, preferably from 3 to 35%, and more preferably from 5 to 30% by weight, based on the total content of the composition, of at least one compound of formula (I) as above defined; and c) from 0 to 20% by weight, preferably from 0 to 15%, and more preferably from 0.2 to 15% by weight, based on the total content of the composition, of an accelerator and/or of a coinitiator.

Preferably, said at least one compound (b) is present in an amount from 5 to 30%, for instance 10, 15, 20, 25 or 30%.

According to the present invention, the terms "photocuring" and "photopolymerizing" and related terms, are synonyms.

The expression "based on the total content of the composition" means that the % weight amounts of any of the components is calculated with respect to the sum of the weight of all the components of the composition, including any possible further additional components (in addition to a), b) and c) above), but possible water and/or solvents which may be present in the composition are not considered for the calculation of said % weight amounts.

According to another of its aspects, the present invention relates to a process for photocuring photopolymerizable compositions coatings, adhesives and inks, which process comprises:

i. providing a photopolymerizable composition as above defined;
ii. coating or printing said photopolymerizable composition onto a substrate, and
iii. photocuring said coated or printed composition with a light source on said substrate.

According to another of its aspects, the present invention relates to a process for three-dimensional printing which comprising photocuring with a light source a mixture comprising the composition as above defined.

According to another of its aspects, the present invention relates to an article of manufacture obtained by the process of the invention.

The photocurable compositions of the present invention can also comprise one or more of the following components: (d) sensitizers and/or (e) further photoinitiators and/or (f) conventional additives, in addition to compounds (a), (b) and, when present, (c).

According to a preferred embodiment, the photopolymerizable composition used the processes of the invention comprises at least components (a), (b), (c), more preferably at least (a), (b), (c), and (d) as above defined.

The photoinitiators of the invention can be used in photocurable compositions comprising ethylenically unsaturated compounds (a). Said unsaturated compounds (a) can contain one or more olefinic double bonds.

They can be low-molecular weight (monomeric) or high-molecular weight (oligomeric) compounds.

Examples of suitable low molecular weight monomers (monomeric compounds) having one double bond are alkyl or hydroxyalkyl acrylates or methacrylates, such as methyl-, ethyl-, butyl-, 2-ethylhexyl-,2-hydroxyethyl- or isobornyl-acrylate; and methyl or ethyl methacrylate.

Further examples are resins modified with silicon or fluorine, e.g. silicone acrylates. Further examples of these monomers are acrylonitrile, acrylamide, methacrylamide, N-substituted (meth)acrylamides, styrene, alkylstyrenes and halogeno styrenes, vinyl esters such as vinyl acetate, vinyl ethers such as iso-butyl vinyl ether, N-vinylpyrrolidone, vinyl chloride or vinylidene chloride.

Examples of monomers having more than one double bond are the ethylene glycol diacrylate, propylene glycol diacrylate, neopentyl glycol diacrylate, hexamethylene glycol diacrylate, bisphenol A diacrylate, 4,4'-bis-(2-acryloyloxyethoxy)-diphenylpropane, trimethylolpropane triacrylate, pentaerythritol triacrylate or tetraacrylate, vinyl acrylate, divinyl benzene, divinyl succinate, diallyl phthalate, triallyl phosphate, triallyl isocyanurate or tris-(2-acryloylethyl) isocyanurate.

Examples of high-molecular weight (oligomeric) polyunsaturated compounds are acrylated epoxy resins, acrylated or vinyl-ether- or epoxy-group-containing polyesters, acrylated polyurethanes or acrylated polyethers. Further examples of unsaturated oligomers are unsaturated polyester resins which are usually prepared from maleic acid, phthalic acid and one or more diols and which have molecular weights of from about 500 Da to 3,000 Da. Such unsaturated oligomers can also be referred to as prepolymers.

Examples of compounds (a) which are particularly suitable for the implementation of the present invention, are esters of ethylenically unsaturated carboxylic acids and polyols or polyepoxides, and polymers containing ethylenically unsaturated groups in the chain or in side groups, e.g. unsaturated polyesters, polyamides and polyurethanes and copolymers thereof, alkyl resins, polybutadiene and butadiene copolymers, polyisoprene and isoprene copolymers, polymers and copolymers having (meth)acrylic groups in side chains, as well as mixtures thereof.

Illustrative examples of unsaturated carboxylic acids or anhydrides, useful for the preparation of the above esters, are acrylic acid, methacrylic acid, maleic anhydride, crotonic acid, itaconic acid, cinnamic acid and unsaturated fatty acids such as linolenic acid and oleic acid. Acrylic and methacrylic acid are preferred.

Examples of polyols, which can also be esterified, are aromatic and aliphatic and cycloaliphatic polyols, preferably aliphatic and cycloaliphatic polyols.

Aromatic polyols are, for example, hydroquinone, 4,4'-dihydroxydiphenyl, 2,2-di(4-hydroxyphenyl) propane, as well as novolaks and resoles.

Polyepoxides, which can be esterified, include those based on the said polyols, especially the reaction products between aromatic polyols and epichlorohydrin. Also suitable as polyols are polymers and copolymers that contain hydroxyl groups in the polymer chain or in side groups, for example polyvinyl alcohol and copolymers thereof or polymethacrylic acid hydroxyalkyl esters or copolymers thereof. Further suitable polyols are oligoesters carrying hydroxyl terminal groups.

Examples of aliphatic and cycloaliphatic polyols include alkylenediols containing preferably from 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 Da to 1,500 Da, 1,3-cyclopentanediol, 1,2-, 1,3- or 1,4-cyclohexanediol, 1,4-dihydroxymethyl cyclohexane, glycerol, tris(p-hydroxy-ethyl)amine, trimethylolethane, trimethylolpropane, pentaerythritol, dipentaerythritol and sorbitol.

Further suitable ethylenically unsaturated compounds (a) are unsaturated polyamides obtained from unsaturated carboxylic acids and aromatic, aliphatic and cycloaliphatic polyamines having preferably from 2 to 6, preferably from 2 to 4, amino groups. Examples of such polyamines are: ethylenediamine, 1,2- or 1,3-propylenediamine, 1,2-, 1,3- or 1,4-butylenediamine, 1,5-pentylenediamine, 1,6-hexylenediamine, octylenediamine, dodecylene diamine, 1,4-diaminocyclohexane, isophoronediamine, phenylene diamine, bisphenylenediamine, di-(β-aminoethyl) ether, diethylene triamine, triethylenetetramine and di(β-aminoethoxy)- and di(β-aminopropoxy)ethane. Other suitable polyamines are polymers and copolymers which may contain additional amino groups in the side chain and oligoamides containing amino end groups.

Specific examples of such unsaturated polyamides are methylenebisacrylamide, 1,6-hexamethylene bisacrylamide, diethylenetriamine trismethacrylamide, bis(methacrylamidopropoxy) ethane and N-[(p-hydroxyethoxy)ethyl]-acrylamide.

Unsaturated polyurethanes are also suitable for the implementation of the present invention as components (a), for example those derived from saturated or unsaturated diisocyanates and unsaturated or saturated diols. Polybutadiene and polyisoprene and copolymers thereof may also be used. Suitable monomers include, for example, olefins, such as ethylene, propene, butene and hexene, (meth)acrylates, acrylonitrile, styrene and vinyl chloride.

Polymers having unsaturated (meth)acrylate groups in the side chain can also be used as component (a). They may typically be reaction products of epoxy resins based on novolac with (meth)acrylic acid; homo- or copolymers of vinyl alcohol or hydroxyalkyl derivatives thereof that have been esterified with (meth)acrylic acid; and homo- and co-polymers of (meth)acrylates that have been esterified with hydroxyalkyl (meth)acrylates.

According to a preferred embodiment, the photocurable composition further comprises a coinitiators (c), also referred to as accelerators.

Suitable examples of accelerators/coinitiators (c) are alcohols, thiols, thioethers, amines or ethers that have an available hydrogen, bonded to a carbon adjacent to the heteroatom, disulfides and phosphines, e.g. as described in EP 438 123 and GB 2 180 358.

Suitable examples of amine accelerators/co-initiators include, but are not limited to, aliphatic, cycloaliphatic, aromatic, aryl-aliphatic, heterocyclic, oligomeric or polymeric amines. They can be primary, secondary or tertiary amines, for example butyl amine, dibutyl amine, tributyl amine, cyclohexyl amine, benzyldimethyl amine, di-cyclohexyl amine, N-phenyl glycine, triethyl amine, phenyl-diethanol amine, triethanolamine, piperidine, piperazine, morpholine, pyridine, quinoline, esters of dimethylamino benzoic acid, Michler's ketone (4,4'-bis-dimethyl aminobenzophenone) and derivatives thereof.

As the amine accelerators/co-initiators, an amine-modified acrylate compound can be used; examples of such amine-modified acrylate include acrylates modified by reaction with a primary or secondary amine that are described in U.S. Pat. No. 3,844,916, EP 280222, U.S. Pat. No. 5,482,649 or U.S. Pat. No. 5,734,002.

Multifunctional amine and polymeric amine derivatives are also suitable as co-initiators some examples are Omnipol® ASA from IGM Resins B.V., Genopol® AB-2 from Rahn A.G., Speedcure® 7040 from Lambson Limited or those described in US2013/0012611.

The photocurable compositions of the present invention can also be formulated in compositions further comprising water and/or solvents, such as organic solvents.

Photosensitizers (d) can be present in an amount comprised between 0.01 and 15% by weight, based on the total content of the composition, preferably between 0.01 and 10% by weight.

Examples of sensitizers are those commonly used in the art, aromatic carbonyl compounds, e.g. benzophenones, thioxanthones, anthraquinones, coumarins and 3-acylcoumarin derivatives, terphenyls, styryl ketones, and 3-(aroylmethylene)-thiazolines, camphorquinones and also eosin, rhodamine and erythrosine dyes.

Examples of thioxanthones are thioxanthone, 2-isopropyl thioxanthone, 2-chloro thioxanthone, 2-dodecyl thioxanthone, 2,4-diethyl thioxanthone, 2,4-dimethyl thioxanthone, 1-methoxycarbonyl thioxanthone, 2-ethoxycarbonyl thioxanthone, 3-(2-methoxyethoxycarbonyl) thioxanthone, 4-butoxycarbonyl thioxanthone, 3-butoxycarbonyl-7-methyl thioxanthone, 1-cyano-3-chloro thioxanthone, 1-ethoxycarbonyl-3-chloro thioxanthone, 1-ethoxycarbonyl-3-ethoxy thioxanthone, 1-ethoxycarbonyl-3-amino thioxanthone, 1-ethoxycarbonyl-3-phenylsulfuryl thioxanthone, 3,4-di[2-(2-methoxyethoxy)ethoxycarbonyl]thioxanthone, 1-ethoxycarbonyl-3-(1-methyl-1-morpholinoethyl) thioxanthone, 2-methyl-6-dimethoxymethyl thioxanthone, 2-methyl-6-(1,1-dimethoxybenzyl) thioxanthone, 2-morpholinomethyl thioxanthone, 2-methyl-6-morpholinomethyl thioxanthone, N-allylthioxanthone-3,4-dicarboximide, N-octylthioxanthone-3,4-dicarboximide, N-(1,1,3,3-tetramethylbutyl)-thioxanthone-3,4-dicarboximide, 1-phenoxy thioxanthone, 6-ethoxycarbonyl-1-2-methoxythioxanthone, 6-ethoxycarbonyl-2-methylthioxanthone, thioxanthone-2-polyethylene glycol ester, 2-hydroxy-3-(3,4-dimethyl-9-oxo-9H-thioxanthon-2-yloxy)-N,N,N-trimethyl-1-propanaminium chloride, or those described in the patent application PCT/EP2011/069514, such as n-dodecyl-7-methyl-thioxanthone-3-carboxylate and N,N-disobutyl-7-methyl-thioxanthone-3-carbamide. Also suitable are polymeric thioxanthone derivatives (e.g. Omnipol® TX from IGM Resins B.V., Genopol® TX-1 from Rahn A.G., Speedcure® 7010 from Lambson Limited).

Example of benzophenones are benzophenone, 4-phenyl benzophenone, 4-methoxy benzophenone, 4,4'-dimethoxybenzophenone, 4,4'-dimethyl benzophenone, 4,4'-dichloro benzophenone, 4,4'-dimethylamino benzophenone, 4,4'-diethylamino benzophenone, 4-methyl benzophenone, 2,4,6-trimethyl benzophenone, 4-(4-methylthiophenyl) benzophenone, 3,3'-dimethyl-4-methoxy benzophenone, methyl 2-benzoyl benzoate, 4-(2-hydroxyethylthio) benzophenone, 4-(4-tolylthio) benzophenone, 4-benzoyl-N,N,N-trimethylbenzene methanaminium chloride, 2-hydroxy-3-(4-benzoylphenoxy)-N,N,N-trimethyl-1-propanaminium chloride monohydrate, 4-(13-acryloyl-1,4,7,10,13-pentaoxatridecyl) benzophenone, 4-benzoyl-N,N-dimethyl-N-[2-(1-oxo-2-propenyl)oxylethyl-benzene methanaminium chloride, or those described in U.S. Pat. No. 9,938,231 (e.g. Omnirad® 991 from IGM Resins B.V.).

Also suitable are polymeric benzophenone derivatives (e.g. Omnipol® BP, Omnipol® 2702 and Omnipol® 682 all from IGM Resins B.V., Genopol® BP-2 from Rahn A.G. and Speedcure® 7005 from Lambson Limited).

Examples of 3-acylcoumarin derivatives are 3-benzoyl coumarin, 3-benzoyl-7-methoxy coumarin, 3-benzoyl-5,7-di(propoxy) coumarin, 3-benzoyl-6,8-dichloro coumarin, 3-benzoyl-6-chloro coumarin, 3,3'-carbonyl-bis[5,7-di (propoxy) coumarin], 3,3'-carbonyl-bis(7-methoxy coumarin), 3,3'-carbonyl-bis(7-diethylamino coumarin), 3-isobutyroyl coumarin, 3-benzoyl-5,7-dimethoxy coumarin, 3-benzoyl-5,7-diethoxy coumarin, 3-benzoyl-5,7-dibutoxy coumarin, 3-benzoyl-5,7-di(methoxyethoxy) coumarin, 3-benzoyl-5,7-di(allyloxy) coumarin, 3-benzoyl-7-dimethylamino coumarin, 3-benzoyl-7-diethylamino coumarin, 3-isobutyroyl-1,7-dimethylamino coumarin, 5,7-dimethoxy-3-(1-benzoyl) coumarin, 5,7-dimethoxy-3(1-benzoyl)-coumarin, 3-benzoylbenzo [f]coumarin, 7-diethylamino-3-thienoyl coumarin, 3-(4-cyanobenzoyl)-5,7-dimethoxy coumarin, or those described in EP2909243 and WO2017216699.

Examples of 3-(aroylmethylene) thiazolines are 3-methy-1,2-benzoylmethylene-β-benzo thiazoline, 3-methyl-2-benzoylmethylene-benzo thiazoline, 3-ethyl-2-propionylmethylene-β-benzo thiazoline.

Examples of other aromatic carbonyl compounds are acetophenone, 3-methoxyacetophenone, 4-phenylacetophenone, benzyl, such as the one described in WO 2013/164394, 2-acetylnaphthalene, 2-naphthaldehyde, 9,10-anthraquinone, 9-fluorenone, dibenzosuberone, xanthone, 2,5-bis(4-diethylaminobenzylidene) cyclopentanone, α-(para-dimethylamino benzylidene), ketones, such as 2-(4-dimethylamino-benzylidene)-indan-1-one or 3-(4-dimethylaminophenyl)-1-indan-5-yl-propenone, 3-phenylthiophthalimide, N-methyl-3,5-di(ethylthio)phthalimide.

Particularly preferred are thioxanthones, coumarins and 3-acylcoumarins. It was observed that the above components (d) increase the activity of photoinitiators (b) without shortening the shelf life of the compositions. Moreover, such compositions have the special advantage that an appropriate choice of the sensitizer (d) allows the spectral sensitivity of photoinitiator (b) to be shifted to any desired wavelength region. The skilled in the art is able to select the suitable sensitizer (d) to make the photoinitiator(s) (b) work at any desired wavelength region.

The further possible photoinitiators (e) can be present in an amount comprised between 0.5 and 15% by weight, of the total content of the composition, preferably between 1 and 10% by weight of the composition.

Examples of other suitable photoinitiators (e) are camphorquinone, benzophenone, benzophenone derivatives, acetophenone, acetophenone derivatives, dialkoxyacetophenones, α-hydroxyketones, α-aminoketones, 4-aroyl-1,3-dioxolanes, benzoin alkyl ethers and benzyl ketals, e.g. benzyl dimethyl ketal, ketosulfones, e.g 1-[4-[(4-benzoyl-phenyl)-thio]-phenyl]-2-methyl-2-[(4-methyl-phenyl)-sulfonyl]-propan-1-one (Esacure® 1001, from IGM Resins B.V.), 3-ketocoumarins, for example as described in EP2909243 and WO2017216699, phenylglyoxylates and derivatives thereof, dimeric phenyl glyoxylates, peresters, e.g. benzophenonetetracarboxylic acid peresters, for example as described in EP 126 541, acylphosphine photoinitiators (which can be selected from mono-acylphosphine oxides, bis-acylphosphine oxides, tris-acylphosphine oxides and multifunctional mono- or bisacylphosphine oxides), halomethyltriazines, hexaaryl bisimidazole/coinitiator systems, e.g. ortho-chlorohexaphenylbisimidazole in combination with 2-mercaptobenzothiazole, ferrocenium compounds or titanocenes, for example dicyclopentadienyl-bis(2,6-difluoro-3-pyrrolo-phenyl)titanium, O-acyloxime ester photoinitiators.

Examples of α-hydroxyketones and α-aminoketones are 1-hydroxy cyclohexylphenyl ketone, 2-hydroxy-2-methyl-1-phenyl-propane-1-one, 1-[4-(2-hydroxyethoxy)phenyl]-2-hydroxy-2-methyl-1-propane-1-one, 2-hydroxy-1-{4-[4-(2-hydroxy-2-methyl-propionyl)-benzyl]phenyl}-2-methyl-propane-1-one), 2-hydroxy-1-{4-[4-(2-hydroxy-2-methyl-propionyl)-phenoxy]-phenyl}-2-methyl-propan-1-one, 2-methyl-1-(4-methylthiophenyl)-2-morpholinopropane-1-one), 2-benzyl-2-dimethylamino-1-(4-morpholinophenyl)-butane-1-one, and (2-(dimethylamino)-2-[(4-methylphenyl) methyl]-1-[4-(4-morpholinyl) phenyl]-1-butanone).

Examples of O-acyloxime ester photoinitiators are 1,2-octanedione,1-[4-(phenylthio)phenyl]-2-(O-benzoyloxime), ethanone 1-[9-ethyl-6-(2-methylbenzoyl)-9H-carbazole-3-yl]1-(O-acetyloxime) or those described in GB 2339571.

Examples of acylphosphine photoinitiators include, but are not limited to, bis(2,4,6-trimethylbenzoyl)phenylphosphine oxide, bis(2,6-dimethoxybenzoyl)-2,4,4-trimethylpentyl phosphine oxide, bis(2,4,6-trimethylbenzoyl)-(2,4-dipentyloxyphenyl), 2,4,6-trimethylbenzoyl-diphenyl phosphine oxide and ethyl (2,4,6-trimethylbenzoyl) phenylphosphinate, Phenyl(2,4,6-trimethylbenzoyl)phosphinic acid, glycerol ethoxylated trimester (Omnipol® TP from IGM Resins B.V.).

Examples of the halomethyltriazines based photoinitiators are 2-[2-(4-methoxy-phenyl)-vinyl]-4,6-bis-trichloromethyl [1,3,5]triazine, 2-(4-methoxy-phenyl)-4,6-bis-trichloromethyl [1,3,5]triazine, 2-(3,4-dimethoxyphenyl)-4,6-bis-trichloromethyl [1,3,5]triazine, 2-methyl-4,6-bis-trichloromethyl [1,3,5]triazine.

Cationic photoinitiators can be also used as the further photoinitiators (e), when the photocurable compositions according to the invention are used in hybrid systems (which in this connection mean mixtures of free-radically and cationically curing systems). Examples of suitable cationic photoinitiators are aromatic sulfonium, phosphonium or iodonium salts, as described e.g. in U.S. Pat. No. 4,950,581, or cyclopentadienylarene-iron(II) complex salts, e.g. ($\eta^6$-isopropylbenzene)($\eta^5$-cyclopentadienyl) iron(II) hexafluorophosphate or photolatent acids based on oximes, as described, for example, in GB 2 348 644, U.S. Pat. Nos. 4,450,598, 4,136,055, WO 00/10972 and WO 00/26219.

The photocuring composition according to the invention may also comprise conventional additives, from 0 to 10% based on the total content of the composition. Additives (f) can be, for example, thermal initiators, binders, stabilizers, and mixture thereof.

The choice of additives is governed by the field of use in question and the properties desired for that field. The additives (f) described above are known in the art and are accordingly used in the amounts conventionally used in the art.

For instance, especially in the case of pigmented compositions, the composition may also comprise, as additional additive (f), a thermal initiator, a compound that forms free radicals when heated, e.g. an azo compounds, such as 2,2'-azobis(4-methoxy-2,4-dimethylvaleronitrile), a triazene, diazosulfide, pentazadiene or a peroxy compound, for example a hydroperoxide or peroxycarbonate, e.g. tert-butyl hydroperoxide, as described e.g. in EP 245 639.

Binders may also be added to the photocurable composition of the invention. The addition of binders is particularly advantageous when the photocurable compounds are liquid or viscous substances. The amount of binder may be, for example, from 5 to 60% by weight, preferably from 10 to 50% by weight, based on the total content of the composition, excluding possible water and solvents. The choice of binder is made in accordance with the field of use and the properties required therefor, such as developability in aqueous and organic solvent systems, adhesion to substrates and sensitivity to oxygen.

Suitable binders are, for example, polymers having a weight average molecular weight (Mw) of approximately from 5,000 Da to 2,000,000 Da, preferably from 10,000 Da to 1,000,000 Da. Illustrative examples are: homo- and copolymers of acrylates and methacrylates, e.g. copolymers of methyl methacrylate/ethyl acrylate/methacrylic acid, poly (methacrylic acid alkyl esters), poly(acrylic acid alkyl esters); cellulose esters and ethers, such as cellulose acetate, cellulose acetate butyrate, methylcellulose, ethylcellulose, polyvinylbutyral, polyvinylformal, cyclised rubber, polyethers such as polyethylene oxide, polypropylene oxide, polytetrahydrofuran, polystyrene, polycarbonates, polyurethanes, chlorinated polyolefins, e.g. polyvinyl chloride, co-polymers of vinyl chloride/vinylidene chloride, co-polymers of vinylidene chloride with acrylonitrile, methyl methacrylate and vinyl acetate, polyvinyl acetate, co-poly (ethylene/vinyl acetate), polymers such as polycaprolactam and poly (hexamethylene adipamide), polyesters such as poly(ethylene glycol terephthalate) and poly(hexamethylene glycol succinate).

Suitable stabilizers are, for example, thermal inhibitors, such as hydroquinone, hydroquinone derivatives, p-methoxyphenol, β-benzol or sterically hindered phenols, e.g. 2,6-di(tert-butyl)-p-cresol, which prevent premature polymerization. In order to increase dark storage stability it is possible to use, for example, copper compounds, such as copper naphthenate, stearate or octoate, phosphorus compounds, for example triphenylphosphine, tributylphosphine, triethyl phosphite, triphenyl phosphite or tribenzyl phosphite, quaternary ammonium compounds, e.g. tetramethylammonium chloride or trimethylbenzylammonium chloride, or hydroxylamine derivatives, e.g. N,N-diethylhydroxylamine. For the purpose of excluding atmospheric oxygen during polymerization it is possible to add paraffin or similar wax-like substances which, being insoluble in the polymer, migrate to the surface at the beginning of the polymerization and form a transparent surface layer which prevents air from entering.

It is also possible to add a light stabilizer, such as UV absorbers, e.g. hydroxyphenylbenzotriazole, hydroxyphenylbenzophenone, oxalic acid amide or hydroxyphenyl-s-triazine type. Such components can be used on their own or in the form of mixtures, with or without the use of sterically hindered amines (HALS).

The photocurable compositions according to the invention may also comprise, as further additives (f), photoreducible dyes, e.g. a xanthene, benzoxanthene, benzothioxanthene, thiazine, pyronin, porphyrin or acridine dye, and/or radiation cleavable trihalomethyl compounds. These compounds are described, for example, in EP445624.

Further customary additives (f) are, depending upon the intended use, optical brighteners, fillers, pigments, both white and colored pigments, colorants, antistatics, wetting agents or flow improvers. Additives conventionally used in the art, e.g. antistatics, flow improvers and adhesion enhancers, can also be used.

In addition to the above components, other components may be present in the composition of the invention.

It is also possible for chain-transfer reagents conventionally used in the art to be added to the compositions according to the invention. Examples are mercaptans, amines and benzothiazole.

The composition of the invention may also comprise colorants and/or colored pigments. Depending upon the intended use, both inorganic and organic pigments may be used. Such additives are well known to the person skilled in the art; some examples are carbon black, iron oxides, such as iron oxide yellow, iron oxide red, chromium yellow, chromium green, nickel titanium yellow, ultramarine blue, cobalt blue, bismuth vanadate, cadmium yellow and cadmium red. Examples of organic pigments are mono- or bis-azo pigments, and also metal complexes thereof, phthalocyanine pigments, polycyclic pigments, e.g. perylene, anthraquinone, thioindigo, quinacridone or triphenylmethane pigments, and also diketo-pyrrolo-pyrrole, isoindolinone, e.g. tetrachloroisoindolinone, isoindoline, dioxazine, benzimidazolone and quinophthalone pigments. The pigments may be used in the formulations on their own or in admixture.

Depending upon the intended use, the pigments can be added to the formulations in amounts conventionally used in the art, for example in an amount from 0.1 to 30% by weight or from 10 to 25% by weight, based on the total weight of the composition.

The composition may also comprise, for example, organic colorants of an extremely wide variety of classes. Examples are azo dyes, methine dyes, anthraquinone dyes and metal complex dyes. Usual concentrations are, for example, from 0.1 to 20% wt, especially from 1 to 5% wt, based on the total weight of the composition.

The photocurable compositions of the invention may comprise water.

The photocurable compositions of the invention are suitable for various purposes, for example as a printing ink, such as screen printing inks, flexographic printing inks, offset printing inks and inkjet printing inks, as clearcoats, as colored coats, for example for wood or metal, as powder coatings, as coating materials inter alia for paper, wood, metal or plastics, as daylight-curable paints for marking structures and roads, for photographic reproduction processes, for holographic recording materials, for image-recording processes or in the production of printing plates that can be developed using organic solvents or using aqueous-alkaline media, for the production of masks for screen printing, as dental filling compounds, as adhesives, as pressure-sensitive adhesives, as laminating resins, as photoresists, e.g. galvanoresists, as etch resists or permanent resists, both liquid and dry films, as photostructurable dielectrics, and as solder masks for electronic circuits, as resists in the production of color filters for any type of display screen or in the creation of structures during the manufacture of plasma displays and electroluminescent displays, in the production of optical switches, optical gratings (interference gratings), in the manufacture of three-dimensional articles by bulk curing (UV curing in transparent moulds) or according to the stereolithography process, as described, for example, in U.S. Pat. No. 4,575,330, in the manufacture of composite materials (e.g. styrene polyesters which may include glass fibers and/or other fibers and other adjuvants) and other methods of printing in three dimensions well-known to one skilled in the art, in the coating or sealing of electronic components or as coatings for optical fibers.

The photocurable compositions of the invention are also suitable for the production of optical lenses, e.g. contact lenses or Fresnel lenses, in the manufacture of medical apparatus, aids or implants, in dry film paints.

The photocurable compositions of the invention are also suitable for the preparation of gels having thermotropic properties. Such gels are described for example in DE 19700064 and EP 678534.

An article comprising a compound of formula (I), or comprising a photocurable composition of the invention, represents a further subject-matter of the invention.

The compounds and compositions according to the invention may also be used as free-radical photoinitiators or photoinitiating systems for radiation-curable powder coatings.

The photocurable compositions according to the invention are suitable, for example, as coating materials for all kinds of substrate, for example wood, textiles, paper, ceramics, glass, plastics, such as polyesters, polyethylene terephthalate, polyolefins and cellulose acetate, especially in the form of films, and also metals, such as Al, Cu, Ni, Fe, Zn, Mg or Co and GaAs, Si or $SiO_2$, to which a protective layer is to be applied or an image is to be applied e.g. by imagewise exposure.

A large number of the most varied kinds of light source may be used in the process according to the invention, the light source emitting at wavelengths from approximately 200 nm to approximately 800 nm. Both point sources and planiform radiators (lamp carpets) are suitable.

Examples are: carbon arc lamps, xenon arc lamps, medium pressure, high pressure and low pressure mercury arc radiators, doped, where appropriate, with metal halides (metal halide lamps), microwave-excited metal vapour lamps, excimer lamps, superactinic fluorescent tubes, fluorescent lamps, argon incandescent lamps, flash lamps, photographic floodlight lamps, light-emitting diodes (LED), electron beams, X-rays and lasers.

According to one embodiment, said light source comprises UV light in at least one of the UVA, UVB and UVC ranges.

According to a preferred embodiment, said light source is a LED source, particularly preferred are LED light source emitting at wavelengths comprised between 365 nm and 420 nm, more preferably at 365 nm, 385 nm and 395 nm.

According to the invention the distance between the lamp and the substrate to be exposed may vary according to the intended use and the type and strength of the lamp, e.g. from 0.1 cm to 150 cm, preferably from 1 cm to 50 cm.

Said photopolymerizable composition may also be applied over a substrate already comprising a coated or printed layer. Said photopolymerizable composition may, after photopolymerization with said light source, be overprinted or overcoated with one or more compositions suitable for printing or coating.

The article obtained by applying said photopolymerizable composition to said substrate by said means of coating or printing, and photopolymerizing by said light source, with or without further elaboration of the article by further coating or printing, represents a further subject-matter of this invention.

As said, we surprisingly found that compounds of formula (I) have a very high reactivity under UVA, UVB and UVC wavelength maintaining a low post cure yellowing compared to that of the prior art. The new compounds showed their great improvement in surface curing under LED and Hg lamps.

The invention is illustrated in detail below by the following examples, which are illustrative and not limiting.

EXPERIMENTAL SECTION

In all the present specification, in case of inconsistences between a chemical name and a chemical formula, the latter prevails.

The expression "r.t." means "room temperature".

In the following formulae, each "n" value is independently selected from the others, i.e. each n value may be different from one another also in the same formula.

In the following Examples, the portion of formula (I) within the square brackets, i.e.

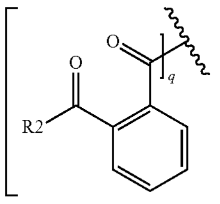

is referred to as "q-moiety".

$^1$H NMR spectra were recorded with a Bruker Ascend 300 MHz NMR Spectrometer.

Preparation 1

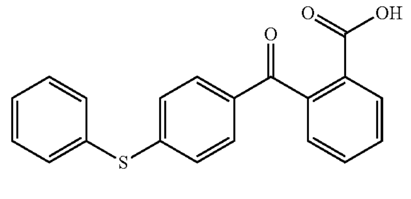 [SMILES: O=C(O)c1ccccc1C(=O)c1ccc(Sc2ccccc2)cc1]

To an ice-cooled mixture of 50.00 g (268.43 mmol) of diphenyl sulfide and 39.76 g (268.43 mmol) of phthalic anhydride in 300 mL of chlorobenzene, 71.58 g (536.82 mmol) of anhydrous aluminum chloride were cautiously added in portions. The reaction mixture was stirred at room temperature for 1.5 hours and then poured into ice/dilute hydrochloric acid. The mixture was extracted with ethyl acetate and the organic layer was separated, washed with 1M hydrochloric acid, dried over anhydrous sodium sulfate, filtered, and the solvent removed by distillation under vacuum. The crude was purified by crystallization from toluene, obtaining 76.63 g of a white solid (yield 86%).

$^1$H-NMR (DMSO-$d_6$, δ ppm): 7.24 (d, 2H), 7.40 (dd, 1H), 7.46-7.56 (m, 7H), 7.61-7.74 (m, 2H), 7.99 (dd, 1H).

Preparation 2

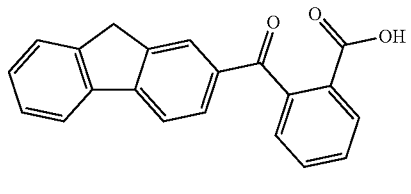 [SMILES: O=C(O)c1ccccc1C(=O)c1ccc2c(c1)Cc1ccccc1-2]

To an ice-cooled mixture of 15.00 g (90.242 mmol) of fluorene and 13.36 g (90.197 mmol) of phthalic anhydride in 270 mL of chlorobenzene, 24.07 g (180.516 mmol) of anhydrous aluminum chloride were cautiously added in portions. The reaction mixture was stirred at room temperature for 1.5 hours and then poured into ice/dilute hydrochloric acid. The semisolid product thus obtained was treated with 270 mL of ethyl acetate, and the resulting solid was filtered off. The filtrate layers were then separated and the organic one was further washed with 1M hydrochloric acid, dried over anhydrous sodium sulfate, filtered, and the solvent removed by distillation under vacuum. The crude, together with the previously filtered off solid, was suspended in 200 mL of toluene and washed under reflux and vigorous stirring for 30 minutes. The mixture was then allowed to cool to r.t. and filtered to obtain 27.26 g of product as a white solid (yield 96%).

$^1$H-NMR (DMSO-$d_6$, δ ppm): 3.99 (s, 2H), 7.38-7.48 (m, 3H), 7.60-7.76 (m, 4H), 7.86 (s, 1H), 7.98-8.04 (m, 3H).

Preparation 3

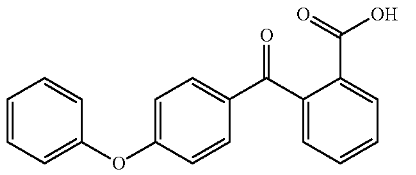 [SMILES: O=C(O)c1ccccc1C(=O)c1ccc(Oc2ccccc2)cc1]

To an ice-cooled mixture of 15.00 g (88.126 mmol) of diphenyl ether and 13.05 g (88.104 mmol) of phthalic anhydride in 250 mL of chlorobenzene, 23.50 g (176.241 mmol) of anhydrous aluminum chloride were cautiously added in portions. The reaction mixture was stirred at room temperature for 1.5 hours and then poured into ice/dilute hydrochloric acid. The mixture was extracted with ethyl acetate and the organic layer was separated, washed with 1M hydrochloric acid, dried over anhydrous sodium sulfate, filtered, and the solvent removed by distillation under vacuum. The crude was purified by crystallization from toluene to obtain 23.25 g of product as a white solid (yield 83%).

$^1$H-NMR (DMSO-$d_6$, δ ppm): 7.03 (d, 2H), 7.14 (m, 2H), 7.25 (m, 1H), 7.38-7.49 (m, 3H), 7.62-7.75 (m, 4H), 7.98 (dd, 1H).

Preparation 4

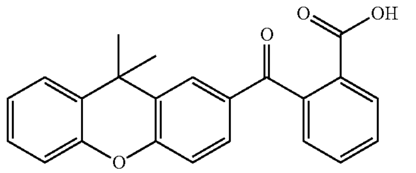 [SMILES: CC1(C)c2ccccc2Oc2ccc(C(=O)c3ccccc3C(=O)O)cc21]

To an ice-cooled mixture of 5.15 g (24.491 mmol) of 9,9-dimethylxanthene and 3.63 g (24.507 mmol) of phthalic anhydride in 85 mL of chlorobenzene, 6.53 g (48.973 mmol) of anhydrous aluminum chloride were cautiously added in portions. The reaction mixture was stirred at room temperature for 1.5 hours and then poured into ice/dilute hydrochloric acid. The mixture was extracted with ethyl acetate and the organic layer was separated, washed with 1M hydrochloric acid, dried over anhydrous sodium sulfate, and filtered. Another equal amount of 4-methoxy phenol was added and the solvent removed by distillation under vacuum. The crude was purified by crystallization from toluene to obtain 7.15 g of product as a white solid (yield 81%).

$^1$H-NMR (DMSO-$d_6$, δ ppm): 1.58 (s, 6H), 7.09-7.20 (m, 3H), 7.28 (m, 1H), 7.38-7.46 (m, 2H), 7.58 (dd, 1H), 7.62-7.78 (m, 2H), 7.93 (d, 1H), 8.00 (dd, 1H).

Preparation 5

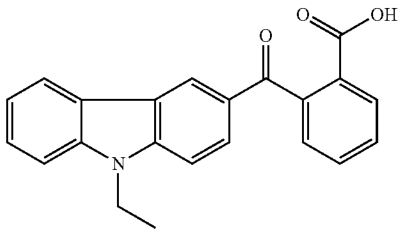 [SMILES: CCn1c2ccccc2c2cc(C(=O)c3ccccc3C(=O)O)ccc21]

To an ice-cooled mixture of 15.00 g (76.817 mmol) of 9-ethylcarbazole and 5.69 g (38.415 mmol) of phthalic anhydride in 250 mL of chlorobenzene, 5.12 g (38.398 mmol) of anhydrous aluminum chloride were cautiously added in portions. The reaction mixture was stirred at room temperature for 1 hour; then the reaction was cooled again and additional 2.84 g (19.174 mmol) of phthalic anhydride and 2.56 g (19.199 mmol) of anhydrous aluminum chloride were added in sequence. This operation was repeated once more. The reaction mixture was finally poured into ice/dilute hydrochloric acid. The mixture was extracted with ethyl acetate and the organic layer was separated, washed with 1M hydrochloric acid, dried over anhydrous sodium sulfate, filtered, and the solvent removed by distillation under vacuum. The crude was suspended in 250 mL of toluene and washed under reflux and vigorous stirring for 30 minutes. The mixture was allowed to cool to r.t. and the solid was collected by filtration. This latter was suspended in 200 mL of toluene and washed again under reflux and vigorous stirring for 24 hours to obtain 7.61 g of product as a white solid (yield 33%).

$^1$H-NMR (DMSO-$d_6$, δ ppm): 1.34 (t, 3H), 4.49 (q, 2H), 7.23 (t, 1H), 7.44-7.55 (m, 2H), 7.64-7.77 (m, 5H), 8.01 (dd, 1H), 8.20 (d, 1H), 8.50 (d, 1H).

Preparation 6

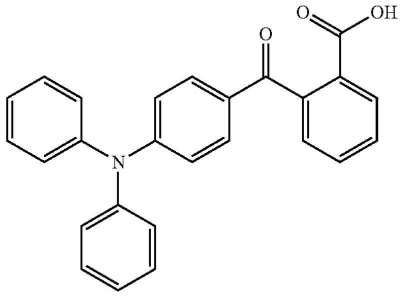 [SMILES: O=C(O)c1ccccc1C(=O)c1ccc(N(c2ccccc2)c2ccccc2)cc1]

To an ice-cooled mixture of 15.00 g (61.145 mmol) of triphenylamine and 4.53 g (30.583 mmol) of phthalic anhydride in 200 mL of chlorobenzene, 4.07 g (30.523 mmol) of anhydrous aluminum chloride were cautiously added in portions. The reaction mixture was stirred at room temperature for 1 hour; then the reaction was cooled again and additional 2.27 g (15.325 mmoles) of phthalic anhydride and 2.04 g (15.299 mmoles) of anhydrous aluminum chloride were added in sequence. This operation was repeated once more. The reaction mixture was finally poured into 400 mL of ice/water. The mixture was extracted with ethyl acetate and the organic layer was separated, dried over anhydrous sodium sulfate, filtered, and the solvent removed by distillation under vacuum. The crude was purified by flash column chromatography on silica gel (toluene/ethyl acetate 50:50) to obtain 7.85 g of product as a yellow solid (yield 34%).

1H-NMR (DMSO-d6, δ ppm): 6.83 (d, 2H), 7.10-7.28 (m, 6H), 7.33-7.43 (m, 5H), 7.49 (d, 2H), 7.56-7.71 (m, 2H), 7.97 (dd, 1H).

Example 1 (Total Grafting 92.3%—q-Moiety/Acrylate 1:2.7)

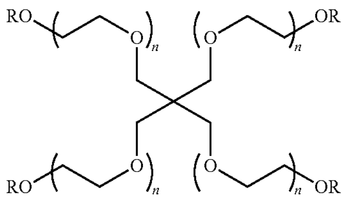

R=

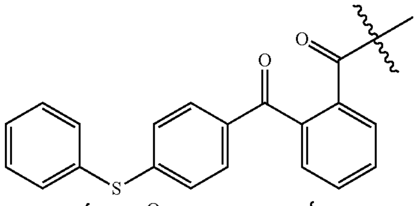

or

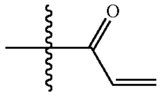

or

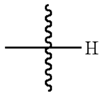

A mixture of 50.00 g (hydroxyl no 634/g) of polyol 4640 (purchased from Perstorp), 47.23 g (141.24 mmol) of the compound of Preparation 1, 3.18 g (23.16 mmol) of a 70% aqueous solution of methanesulfonic acid, and 2.53 g (19.20 mmol) of a 50% aqueous solution of hypophosphorous acid, in toluene was stirred at reflux for 6 h while removing the water by using a Dean-Stark apparatus. Thereafter, the mixture was allowed to reach r.t. and 0.14 g of 4-methoxy phenol, followed by 40.30 g (559.26 mmol) of acrylic acid, were added. The mixture was stirred at 85° C. (internal temperature) by bubbling air inside through a pasteur pipette to induce the reflux, while keeping the temperature constant for 6 h. The mixture was finally allowed to reach r.t., diluted with EtOAc (150 mL), and washed with 0.25 M $Na_2CO_3$ (200 mL) and brine (200 mL). The organic layer was dried over $Na_2SO_4$, and filtered. Another equal amount of 4-methoxy phenol was added and the solvent removed under reduced pressure to obtain 103.50 g of product as a pale-yellow oil (88% yield).

$^1$H-NMR (DMSO-$d_6$, δ ppm): 8.00-7.96 (m, 1H), 7.75-7.32 (m, 12H), 6.23-6.40 (m, 5.3H), 5.98-5.83 (m, 2.7H), 4.22-4.02 (m, 2.8H), 4.26-3.88 (m, 7.4H), 3.68-3.27 (29.6H).

Example 2 (Total Grafting 80.5%—q-Moiety/Acrylate 2.9:1)

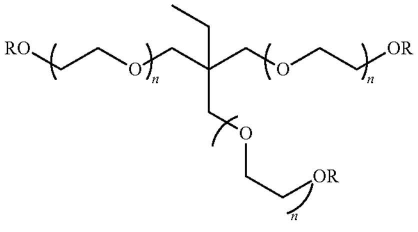

R =

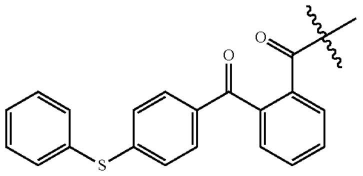

or

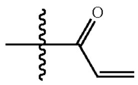

or

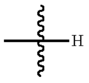

A mixture of 2.50 g (hydroxyl no 364/g) of polyol 3380 (purchased from PERSTORP), 3.36 g (10.87 mmol) of the compound of Preparation 1, 0.09 g (0.66 mmol) of a 70% aqueous solution of methanesulfonic acid, and 0.07 g (0.55 mmol) of a 50% aqueous solution of hypophosphorous acid, in toluene was stirred at reflux for 6 h while removing the water by using a Dean-Stark apparatus. Thereafter, the mixture was allowed to reach r.t. and 0.007 g of 4-methoxy phenol, followed by 0.51 g (7.14 mmol) of acrylic acid, were added. The mixture was stirred at 85° C. (internal temperature) by bubbling air inside through a pasteur pipette to induce the reflux, while keeping the temperature constant for 6 h. The mixture was finally allowed to reach r.t., diluted with EtOAc (50 mL), and washed with 0.25 M $Na_2CO_3$ (25 mL) and brine (25 mL). The organic layer was dried over $Na_2SO_4$, and filtered. Another equal amount of 4-methoxy phenol was added and the solvent removed under reduced pressure to obtain 5.87 g of product as a colorless oil (98% yield).

$^1$H-NMR (DMSO-$d_6$, δ ppm): 8.04-7.88 (m, 1.8H), 7.83-7.62 (m, 4H), 7.60-7.34 (m, 13.7H), 7.32-7.10 (m, 5.6H), 6.39-6.05 (m, 1.2H), 5.99-5.84 (m, 0.6H), 4.26-3.87 (m, 4.9H), 3.65-3.34 (m, 33.1H), 1.43-1.18 (m, 2H), 0.89-0.58 (m, 3H).

Example 3 (Total Grafting 70%—q-Moiety/Acrylate 2.5:1)

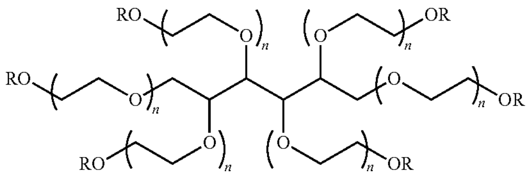

-continued

R =

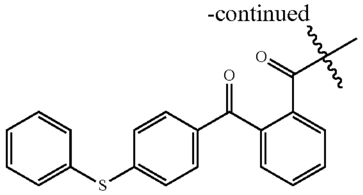

or

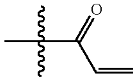

or

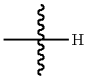

A mixture of 2.50 g (hydroxyl no 300/g) of sorbilene RE/20 (purchased from Lamberti SpA), 2.24 g (6.69 mmol) of the compound of Preparation 1, 0.08 g (0.55 mmol) of a 70% aqueous solution of methanesulfonic acid, and 0.06 g (0.45 mmol) of a 50% aqueous solution of hypophosphorous acid, in toluene was stirred at reflux for 6 h while removing the water by using a Dean-Stark apparatus. Thereafter, the mixture was allowed to reach r.t. and 0.006 g of 4-methoxy phenol, followed by 0.64 g (8.83 mmol) of acrylic acid, were added. The mixture was stirred at 85° C. (internal temperature) by bubbling air inside through a pasteur pipette to induce the reflux, while keeping the temperature constant for 6 h. The mixture was finally allowed to reach r.t., diluted with EtOAc (50 mL), and washed with 0.25 M $Na_2CO_3$ (25 mL) and brine (25 mL). The organic layer was dried over $Na_2SO_4$, and filtered. Another equal amount of 4-methoxy phenol was added and the solvent removed under reduced pressure to obtain 4.51 g of product as a colorless oil (88% yield).

$^1$H-NMR (DMSO-$d_6$, δ ppm): 7.94-7.77 (m, 1H), 7.76-7.03 (m, 12H), 6.31-5.96 (m, 0.8H), 5.91-5.77 (m, 0.4H), 4.17-3.98 (m, 7H), 3.70-3.27 (m, 85H).

Example 4 (Total Grafting 96.8%—1:2.8 q-Moiety/Acrylate)

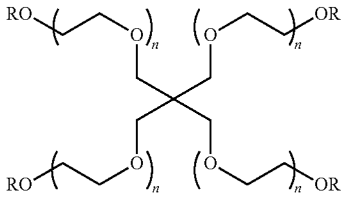

R =

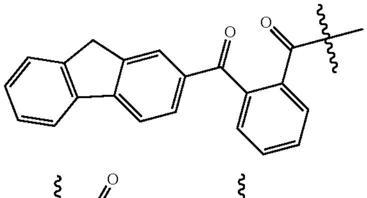

or

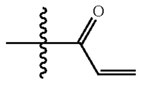

or

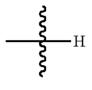

A mixture of 50.00 g (hydroxyl no 634/g) of polyol 4640 (purchased from Perstorp), 44.40 g (141.25 mmol) of the compound of Preparation 2, 3.18 g (23.16 mmol) of a 70% aqueous solution of methanesulfonic acid, and 2.53 g (19.20 mmol) of a 50% aqueous solution of hypophosphorous acid, in toluene was stirred at reflux for 6 h while removing the water by using a Dean-Stark apparatus. Thereafter, the mixture was allowed to reach r.t. and 0.14 g of 4-methoxy phenol, followed by 40.30 g (559.26 mmol) of acrylic acid, were added. The mixture was stirred at 85° C. (internal temperature) by bubbling air inside through a pasteur pipette to induce the reflux, while keeping the temperature constant for 6 h. The mixture was finally allowed to reach r.t., diluted with EtOAc (150 mL), and washed with 0.25 M $Na_2CO_3$ (200 mL) and brine (200 mL). The organic layer was dried over $Na_2SO_4$, and filtered. Another equal amount of 4-methoxy phenol was added and the solvent removed under reduced pressure to obtain 113.76 g of product as a pale-yellow oil (91% yield).

$^1$H-NMR (DMSO-$d_6$, δ ppm): 8.09-7.84 (m, 4H), 7.83-7.55 (m, 4H), 7.54-7.32 (m, 3H), 6.41-6.05 (m, 5.5H), 6.00-5.83 (m, 2.8H), 4.26-3.88 (m, 7.6H), 3.68-3.27 (29.4H).

Example 5 (Total Grafting 90.0%—q-Moiety/Acrylate 1:1.5)

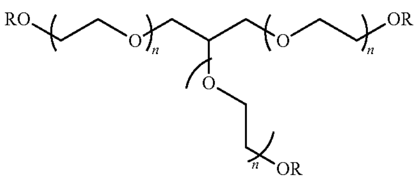

R =

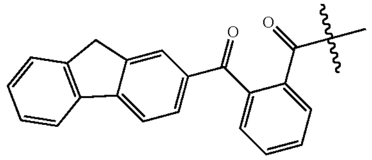

or

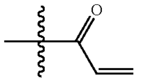

or

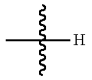

A mixture of 2.50 g (hydroxyl no 370/g) of aionico GL/609 (purchased from Lamberti SpA), 1.86 g (5.44 mmol) of the compound of Preparation 2, 0.09 g (0.68 mmol) of a 70% aqueous solution of methanesulfonic acid, and 0.07 g (0.56 mmol) of a 50% aqueous solution of hypophosphorous acid, in toluene was stirred at reflux for 6 h while removing the water by using a Dean-Stark apparatus. Thereafter, the mixture was allowed to reach r.t. and 0.006 g of 4-methoxy phenol, followed by 1.05 g (14.51 mmol) of acrylic acid, were added. The mixture was stirred at 85° C. (internal temperature) by bubbling air inside through a pasteur pipette to induce the reflux, while keeping the temperature constant for 6 h. The mixture was finally allowed to reach r.t., diluted with EtOAc (50 mL), and washed with 0.25 M $Na_2CO_3$ (25 mL) and brine (25 mL). The organic layer was dried over $Na_2SO_4$, and filtered. Another equal amount of 4-methoxy phenol was added and the solvent removed under reduced pressure to obtain 4.58 g of product as a colorless oil (89% yield).

$^1$H-NMR (DMSO-$d_6$, δ ppm): 8.08-7.85 (m, 4H), 7.83-7.55 (m, 5H), 7.46-7.30 (m, 2H), 6.39-6.09 (m, 2.9H), 5.99-5.84 (m, 1.5H), 4.22-4.16 (m, 2H), 4.15-3.89 (m, 4.8H), 3.69-3.37 (32.2H).

Example 6 (Total Grafting 87.5%—q-Moiety/Acrylate 1:2.5)

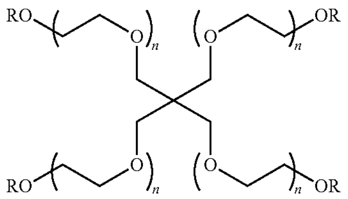

R =

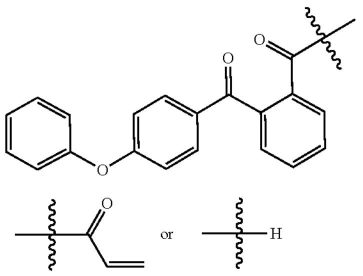

or

A mixture of 2.50 g (hydroxyl no 634/g) of polyol 4640 (purchased from Perstorp), 2.25 g (7.06 mmol) of the compound of Preparation 3, 0.16 g (1.16 mmol) of a 70% aqueous solution of methanesulfonic acid, and 0.13 g (0.96 mmol) of a 50% aqueous solution of hypophosphorous acid, in toluene was stirred at reflux for 6 h while removing the water by using a Dean-Stark apparatus. Thereafter, the mixture was allowed to reach r.t. and 0.007 g of 4-methoxy phenol, followed by 2.01 g (27.97 mmol) of acrylic acid, were added. The mixture was stirred at 85° C. (internal temperature) by bubbling air inside through a pasteur pipette to induce the reflux, while keeping the temperature constant for 6 h. The mixture was finally allowed to reach r.t., diluted with EtOAc (50 mL), and washed with 0.25 M $Na_2CO_3$ (25 mL) and brine (25 mL). The organic layer was dried over $Na_2SO_4$, and filtered. Another equal amount of 4-methoxy phenol was added and the solvent removed under reduced pressure to obtain 4.70 g of product as a colorless oil (81% yield).

$^1$H-NMR (DMSO-$d_6$, δ ppm): 8.04-7.95 (m, 1H), 7.80-7.67 (m, 4H), 7.55-7.7.40 (m, 3H), 7.29-6.95 (m, 5H), 6.40-6.13 (m, 5H), 6.02-5.82 (m, 2.5H), 4.23-4.08 (m, 7H), 3.67-3.30 (m, 21H).

Example 7 (Total Grafting 58.3%—q-Moiety/Acrylate 1:2.5)

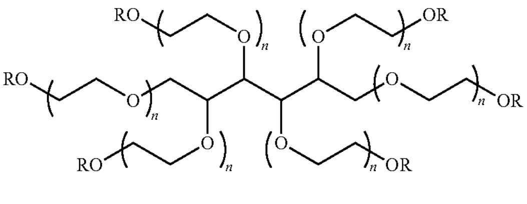

-continued

R =

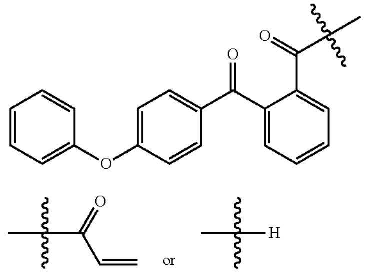

or

A mixture of 3.00 g (hydroxyl no 300/g) of sorbilene RE/20 (purchased from Lamberti SpA), 0.85 g (2.66 mmol) of the compound of Preparation 3, 0.09 g (0.66 mmol) of a 70% aqueous solution of methanesulfonic acid, and 0.07 g (0.55 mmol) of a 50% aqueous solution of hypophosphorous acid, in toluene was stirred at reflux for 6 h while removing the water by using a Dean-Stark apparatus. Thereafter, the mixture was allowed to reach r.t. and 0.004 g of 4-methoxy phenol, followed by 1.27 g (17.59 mmol) of acrylic acid, were added. The mixture was stirred at 85° C. (internal temperature) by bubbling air inside through a pasteur pipette to induce the reflux, while keeping the temperature constant for 6 h. The mixture was finally allowed to reach r.t., diluted with EtOAc (50 mL), and washed with 0.25 M $Na_2CO_3$ (25 mL) and brine (25 mL). The organic layer was dried over $Na_2SO_4$, and filtered. Another equal amount of 4-methoxy phenol was added and the solvent removed under reduced pressure to obtain 3.60 g of product as a colorless oil (80% yield).

$^1$H-NMR (DMSO-$d_6$, δ ppm): 8.03-7.90 (m, 1H), 7.88-7.60 (m, 4H), 7.58-7.7.35 (m, 3H), 7.29-6.92 (m, 5H), 6.40-6.08 (m, 5H), 5.96-5.86 (m, 2.5H), 4.58-4.10 (m, 7H), 3.80-3.38 (m, 85H).

Example 8 (Total Grafting 87%—q-Moiety/Acrylate 1:2.4)

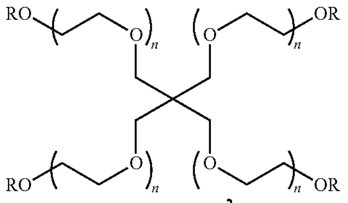

R =

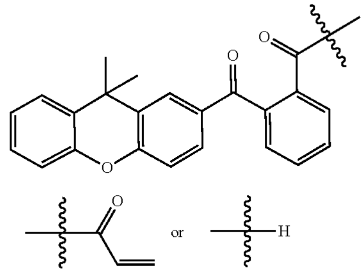

or

A mixture of 2.50 g (hydroxyl no 634/g) of polyol 4640 (purchased from Perstorp), 2.52 g (7.06 mmol) of the compound of Preparation 4, 0.17 g (1.16 mmol) of a 70% aqueous solution of methanesulfonic acid, and 0.13 g (0.96 mmol) of a 50% aqueous solution of hypophosphorous acid, in toluene was stirred at reflux for 6 h while removing the water by using a Dean-Stark apparatus. Thereafter, the mixture was allowed to reach r.t. and 0.007 g of 4-methoxy phenol, followed by 1.69 g (23.44 mmol) of acrylic acid, were added. The mixture was stirred at 85° C. (internal temperature) by bubbling air inside through a pasteur pipette to induce the reflux, while keeping the temperature constant for 6 h. The mixture was finally allowed to reach r.t., diluted with EtOAc (50 mL), and washed with 0.25 M $Na_2CO_3$ (25 mL) and brine (25 mL). The organic layer was dried over $Na_2SO_4$, and filtered. Another equal amount of 4-methoxy phenol was added and the solvent removed under reduced pressure to obtain 5.98 g of product as a colorless oil (96% yield).

$^1$H-NMR (DMSO-$d_6$, δ ppm): 8.03-7.79 (m, 2H), 7.75-7.52 (m, 2H), 7.51-7.7.26 (m, 3H), 7.24-6.90 (m, 4H), 6.32-5.94 (m, 4.5H), 5.91-5.71 (m, 2.4H), 4.18-3.87 (m, 6.7H), 3.65-3.26 (m, 21.3H).

Example 9 (Total Grafting 87.5%—q-Moiety/Acrylate 1:2.5)

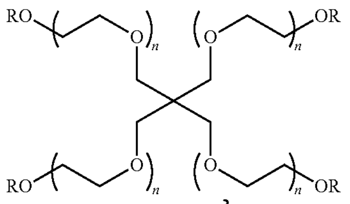

R = 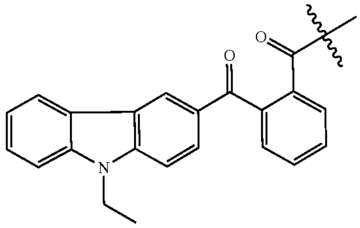 or

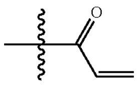 or 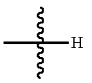

A mixture of 2.50 g (hydroxyl no 634/g) of polyol 4640 (purchased from Perstorp), 2.42 g (7.06 mmol) of the compound of Preparation 5, 0.16 g (1.16 mmol) of a 70% aqueous solution of methanesulfonic acid, and 0.13 g (0.96 mmol) of a 50% aqueous solution of hypophosphorous acid, in toluene was stirred at reflux for 6 h while removing the water by using a Dean-Stark apparatus. Thereafter, the mixture was allowed to reach r.t. and 0.007 g of 4-methoxy phenol, followed by 2.01 g (27.97 mmol) of acrylic acid, were added. The mixture was stirred at 85° C. (internal temperature) by bubbling air inside through a pasteur pipette to induce the reflux, while keeping the temperature constant for 6 h. The mixture was finally allowed to reach r.t., diluted with EtOAc (50 mL), and washed with 0.25 M $Na_2CO_3$ (25 mL) and brine (25 mL). The organic layer was dried over $Na_2SO_4$, and filtered. Another equal amount of 4-methoxy phenol was added and the solvent removed under reduced pressure to obtain 5.64 g of product as a colorless oil (95% yield).

$^1$H-NMR (DMSO-$d_6$, δ ppm): 8.55-8.46 (m, 1H), 8.24-8.12 (m, 1H), 8.07-7.94 (m, 1H), 7.83-7.59 (m, 5H), 7.56-7.42 (m, 2H), 7.22-7.13 (m, 1H), 6.40-6.06 (m, 5H), 5.99-5.82 (m, 2.5H), 4.59-4.36 (m, 2H), 4.26-4.02 (m, 7H), 3.70-3.36 (m, 21H).

Example 10 (Total Grafting 92%—q-Moiety/Acrylate 1:2.7)

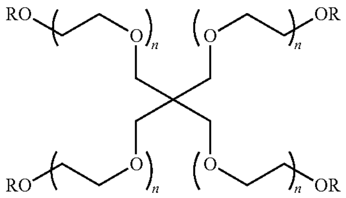

R = 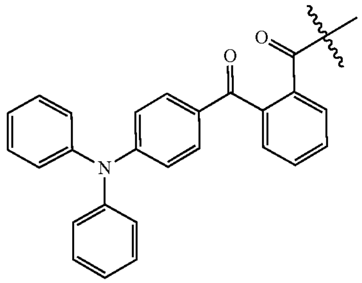 or

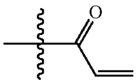 or 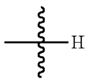

A mixture of 2.50 g (hydroxyl no 634/g) of polyol 4640 (purchased from Perstorp), 2.78 g (7.06 mmol) of LFC4 the compound of Preparation 6, 553, 0.16 g (1.16 mmol) of a 70% aqueous solution of methanesulfonic acid, and 0.13 g (0.96 mmol) of a 50% aqueous solution of hypophosphorous acid, in toluene was stirred at reflux for 6 h while removing the water by using a Dean-Stark apparatus. Thereafter, the mixture was allowed to reach r.t. and 0.007 g of 4-methoxy phenol, followed by 1.69 g (23.44 mmol) of acrylic acid, were added. The mixture was stirred at 85° C. (internal temperature) by bubbling air inside through a pasteur pipette to induce the reflux, while keeping the temperature constant for 6 h. The mixture was finally allowed to reach r.t., diluted with EtOAc (50 mL), and washed with 0.25 M $Na_2CO_3$ (25 mL) and brine (25 mL). The organic layer was dried over $Na_2SO_4$, and filtered. Another equal amount of 4-methoxy phenol was added and the solvent removed under reduced pressure to obtain 5.70 g of product as a colorless oil (89% yield).

$^1$H-NMR (DMSO-$d_6$, δ ppm): 7.91-7.78 (m, 1H), 7.66-7.49 (m, 2H), 7.47-7.7.36 (m, 1H), 7.35-6.97 (m, 12H), 6.96-6.82 (m, 1H), 6.79-6.67 (m, 1H), 6.34-5.95 (m, 5.14H), 5.92-5.72 (m, 2.7H), 4.18-3.98 (m, 7.4H), 3.66-3.22 (m, 20.6H).

Comparative Tests

The activity of representative photoinitiators (PIs) of the invention were compared with the photoinitiator Ebecryl LEO 10103 (marketed by Allnex), herein also referred to as COMP-1.

Example 11

Tack-Free in Clear Formulation and Yellow Index (YI)

The photopolymerizable compositions for the test were prepared by dissolving the PIs at the concentration of 20% by weight in a solution of Photomer 3016 (Bisphenol A epoxy diacrylate) 50%, Photomer 4335 (PETIA) 15%, Photomer 4666 (DPHA) 15%, Photomer 4172 (PPTTA) 20%. The PIs were tested alone (Table 1) or with the addition of a co-initiator (Omnipol ASA) at a concentration of 4% by weight (Table 2) or with the addition of a co-initiator (Omnipol ASA) at a concentration of 4% by weight and of Omnirad ITX as a sensitizer at a concentration of 0.5% by weight (Tables 3 and 4).

The photopolymerizable composition is spread with a thickness of 12 microns on a varnished cardboard using a bar-coater, then the polymerization is carried out using:

a) a Mercury lamp at a distance of 8 cm b) a LED 395 nm lamp at a distance of 0.5 cm c) a LED 365 nm lamp at a distance of 0.5 cm In some tests, YI was also evaluated.

The results are expressed in meters per minutes as the maximum speed at which the tack-free is reached.

In Table 1 the results using UV Hg lamp 120 W/cm are reported

TABLE 1

| PI | Tack-free m/min |
|---|---|
| COMP-1 | 14 |
| Example 1 | 34 |
| Example 3 | 26 |
| Example 6 | 19 |
| Example 9 | 21 |

In Table 2 the results using UV LED 365 lamp 12 W/$cm^2$ are reported (PI+co-initiator)

TABLE 2

| PI | Tack-free m/min |
|---|---|
| COMP-1 | no tack-free achieved |
| Example 1 | 15 |

In Table 3 the results using UV LED 395 lamp 16 W/$cm^2$ are reported (PI+co-initiator+sensitizer)

TABLE 3

| PI | Tack-free m/min | YI |
|---|---|---|
| COMP-1 | 24 | 14.08 |
| Example 1 | 26 | 10.97 |
| Example 6 | n.d. | 8.79 |
| Example 8 | n.d. | 9.04 |

In Table 4 the results using UV LED 365 lamp 12 W/$cm^2$ are reported (PI+co-initiator+sensitizer)

TABLE 4

| PI | Tack-free m/min |
|---|---|
| COMP-1 | 20 |
| Example 1 | 25 |
| Example 3 | 25 |
| Example 4 | 28 |

The above results show that the compounds of the invention are more performant with respect to the Comparative PI in the Tack-free test and/or in the YI test, either using a UV Hg lamp and UV LED lamps.

The invention claimed is:

1. A compound of formula (I)

(I)

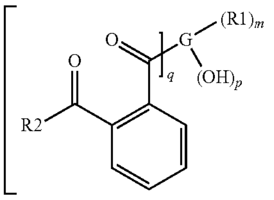

wherein

G is the residue of optionally ethoxylated and/or propoxylated monomeric, oligomeric or polymeric polyols G-(OH) m+q+p;

m is from 1 to 7 q is from 1 to 7;

p is from 0 to 6;

m+q+p is from 3 to 8;

R1 is $CH_2{=}CH{-}C({=}O)$ or $CH_2{=}C(CH_3){-}C({=}O)$;

R2 is selected from (A)

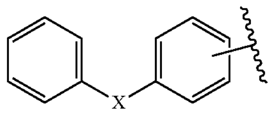

(B)

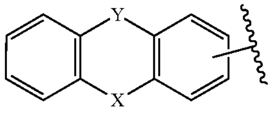

and (C)

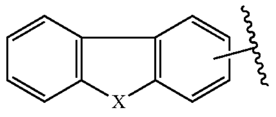

wherein

X is selected from O, S, C(R4)(R5) and NR7;

Y is selected from O, S, C(R4)(R5) and NR6;

R4 and R5 each independently, are selected from H, C1-C12 alkyl, OH and C1-C10 alkoxy;

R6 is selected from H, C1-C8 alky;

R7 is H, C1-C8 alkyl or unsubstituted phenyl;

and the wavy line shows the bonds linking to the keto groups of formula (I).

2. The compound of claim 1, wherein G-$(OH)_{m+q+p}$ is selected from a monomeric polyol, an oligomeric polyol and mixtures thereof, optionally ethoxylated or propoxylated.

3. The compound of claim 1, wherein G-$(OH)_{m+q+p}$ has a number average molecular weight not greater than 1,500 Da, more preferably not greater than 1,000 Da and most preferably not greater than 800 Da; and not lower than 100 Da, preferably not lower than 200 Da.

4. The compound of claim 1, wherein q is from 1 to 4;

p is from 0 to 3;

m is from 1 to 6; and m+q+p is from 3 to 6.

5. The compound of claim 1, wherein R2 is (A) and X is S or O.

6. A photopolymerizable composition comprising:

a) from 50 to 99.9% by weight, based on the total content of the composition of at least one ethylenically unsaturated compound;

b) from 1 to 40% by weight, based on the total content of the composition, of at least one compound of formula (I) as defined in claim 1; and c) from 0 to 20% by weight, based on the total content of the composition, of an accelerator and/or of a coinitiator.

7. The photopolymerizable composition of claim 6, further comprising one or more of the following components:

d) from 0.01 to 15% by weight based on the total content of the composition, of one or more sensitizer; and/or e) from 0.5 to 15% by weight based on the total content of the composition, of one or more further photoinitiators.

8. The photopolymerizable composition of claim 6, wherein said accelerator and/or coinitiator is an amine.

9. A process for photocuring photopolymerizable compositions, coatings, adhesives and inks, which process comprises:

i. providing a photopolymerizable composition as defined in claim 6;

ii. coating or printing said photopolymerizable composition onto a substrate; and iii. photopolymerizing said coated or printed composition on said substrate with a light source.

10. The process of claim 9, wherein said light source comprises UV light in at least one of the UVA, UVB and UVC ranges.

11. The process of claim 9, wherein said light source is a LED source.

12. The process of claim 9, further comprising the step of applying said photopolymerizable composition to a substrate prior to photopolymerizing it.

* * * * *